United States Patent
Kobayashi et al.

[11] Patent Number: 6,155,099
[45] Date of Patent: Dec. 5, 2000

[54] APPARATUS FOR MEASURING QUANTITY OF HYDROGEN

[75] Inventors: Masafumi Kobayashi; Mayumi Kazuta, both of Hokkaido, Japan

[73] Assignee: Kabushiki Kaisha Equos Research, Japan

[21] Appl. No.: 09/337,125

[22] Filed: Jun. 21, 1999

[30] Foreign Application Priority Data

| Jun. 29, 1998 | [JP] | Japan | 10-197996 |
| Jun. 9, 1999 | [JP] | Japan | 11-162279 |

[51] Int. Cl.[7] .......... G01N 21/41; G01N 31/06; G01N 27/12; H01C 7/00
[52] U.S. Cl. .......... 73/31.05; 73/23.2; 422/88; 422/98; 338/34
[58] Field of Search .......... 73/31.05, 31.06, 73/23.2; 422/88, 98, 95; 338/34

[56] References Cited

U.S. PATENT DOCUMENTS

| 3,242,717 | 3/1966 | Matle et al. .......... 73/27 |
| 4,358,951 | 11/1982 | Chang .......... 73/23 |
| 4,443,781 | 4/1984 | Ohta et al. .......... 338/34 |
| 4,453,151 | 6/1984 | Leary et al. .......... 338/34 |
| 4,638,286 | 1/1987 | Nichols .......... 338/34 |
| 4,890,496 | 1/1990 | Birring et al. .......... 73/597 |
| 4,928,521 | 5/1990 | Jardine .......... 73/151 |
| 5,367,283 | 11/1994 | Lauf et al. .......... 338/34 |
| 5,605,612 | 2/1997 | Park et al. .......... 204/429 |
| 5,629,474 | 5/1997 | Williams .......... 73/23.2 |
| 5,719,322 | 2/1998 | Lansbarkis et al. .......... 73/23.39 |
| 5,800,783 | 9/1998 | Nanaumi et al. .......... 422/94 |
| 5,958,787 | 9/1999 | Schönfeld et al. .......... 436/116 |
| 5,969,232 | 10/1999 | Schonauer et al. .......... 73/31.05 |

*Primary Examiner*—Hezron Williams
*Assistant Examiner*—J. David Wiggins
*Attorney, Agent, or Firm*—Lorusso & Loud

[57] ABSTRACT

A sensor is constituted by joining a pair of electrodes to a sensor body formed by binding hydrogen occluding metal with binders. Change in the electric resistance between the electrodes and the quantity of hydrogen occluded by the hydrogen occluding metal in the sensor body has a one to one relationship. Therefore, the quantity of hydrogen occluded by the hydrogen occluding metal can be estimated from the resistance value obtained by the sensor.

32 Claims, 12 Drawing Sheets

APPARATUS FOR MEASURING QUANTITY OF HYDROGEN

BACKGROUND OF THE INVENTION

The present invention relates to an apparatus for measuring the quantity of hydrogen occluded in hydrogen occluding metal.

Hitherto, the quantity of hydrogen occluded in hydrogen occluding metal enclosed in a tank for accumulating hydrogen has been measured by measuring the pressure (the equilibrium pressure of hydrogen) in the tank. In accordance with the measured pressure, the quantity of occluded hydrogen, that is, the quantity of hydrogen stored in the tank has been estimated.

The foregoing method of estimating the quantity of hydrogen by measuring the pressure in the tank cannot accurately measure the quantity of hydrogen because a one-to-one relationship cannot easily be obtained between the pressure in the tank and the quantity of hydrogen.

The hydrogen occluding metal expands when it occludes hydrogen and contracts when hydrogen occluding metal discharges hydrogen. A method of estimating the quantity of hydrogen in the tank for accumulating hydrogen by measuring change in the volume of the hydrogen occluding metal by using the above-mentioned characteristic has been disclosed in Japanese Patent Laid-Open No. 6-249777. The change in the volume of the hydrogen occluding metal in the form of powder cannot be easily and directly measured. Therefore, the foregoing method includes the step of applying pressure to an optical fiber by expansion and contraction of the hydrogen occluding metal to indirectly measure the change in the volume of the hydrogen occluding metal in accordance with the change in light which passes through the optical fiber.

The foregoing method having the step of measuring change in the volume of the hydrogen occluding metal by using light, however, requires a structure which is too complicated.

SUMMARY OF THE INVENTION

An object of the present invention is to provide a novel structure which is capable of overcoming the above-mentioned problem and which measures the quantity of hydrogen occluded in hydrogen occluding metal.

Another object of the present invention is to provide a simple structure for measuring the quantity of hydrogen occluded in the hydrogen occluding metal.

The present invention is capable of achieving at least one of the foregoing objects by providing:

a sensor comprising: a sensor body formed by combining hydrogen occluding metal particles with a binder; and electrodes joined to the sensor body.

The sensor having the above-mentioned structure is arranged such that its electric resistance changes in correspondence to the quantity of hydrogen occluded in the hydrogen occluding metal in the sensor body. The reason for this is estimated as follows.

That is, the hydrogen occluding metal in the form of powder or grains expands or contracts according to the quantity of occluded hydrogen. FIG. 1(A) shows a case in which hydrogen occluding metal 12a of a sensor body 12 has occluded hydrogen in only a small quantity. Since the hydrogen occluding metal 12a is contracted in this case, only a small quantity of the hydrogen occluding metal particles are brought into contact with one another in the binder 12b. Even if the hydrogen occluding metal particles are brought into contact with each other, the contact pressure (adhesion strength) is low. Therefore, the area of contact between the hydrogen occluding metal is reduced, causing the contact resistance to be raised. As a result, the electric resistance of the sensor body 12 is raised if the binder is made of an insulating material or a conductive material.

FIG. 1(B) shows a case in which the hydrogen occluding metal 12a of the sensor body 12 has occluded hydrogen in a large quantity. Since the hydrogen occluding metal 12a is expanded, the amount of contact of the hydrogen occluding metal particles is enlarged. Moreover, the mutual contact resistance is lowered. Therefore, the electric resistance in the state shown in FIG. 1(B) is lowered as compared with the state shown in FIG. 1(A).

The resistance values of the sensor and the quantities of hydrogen in the hydrogen occluding metal have a one-to-one relationship. Therefore, predetermination of the foregoing relationship enables the quantity of hydrogen (a ratio of occluded hydrogen) in the hydrogen occluding metal in the sensor body to be obtained by measuring the resistance of the sensor body through the electrodes. The hydrogen occluding metal in the sensor body and the hydrogen occluding metal in the tank for accumulating hydrogen are the same or the same type. When the hydrogen occluding metal has been disposed in the tank, the quantity of hydrogen per unit hydrogen occluding metal in the sensor body and the quantity of hydrogen per unit hydrogen occluding metal in the tank are substantially the same. Therefore, the quantity of hydrogen in the tank can easily and accurately be estimated in accordance with the ratio of the quantity of the hydrogen occluding metal included in the sensor body and the quantity of the hydrogen occluding metal in the tank for accumulating hydrogen.

The hydrogen occluding metal may be a conventional alloy, such as a Ti—Fe alloy, a Ti—Mn alloy, a La alloy, a Mn alloy or a V-type alloy.

It is preferable that the hydrogen occluding metal for forming the sensor body is the same as the hydrogen occluding metal enclosed in the tank for accumulating hydrogen. The reason for this lies in that the foregoing estimation can be more accurately performed when the hydrogen occluding metal in the sensor body performs the same hydrogen occluding operation as that of hydrogen occluding metal in the tank.

As a matter of course, a case is permitted in which the hydrogen occluding metal in the sensor body are physically (the particle size or the like) and/or chemically (the material or the like) different from each other. If the quantity of hydrogen per unit hydrogen occluding metal in the sensor body and the quantity of hydrogen per unit hydrogen occluding metal in the tank have the one-to-one relationship, the foregoing estimation can be performed.

The particle size of the hydrogen occluding metal is not limited in the present invention. Powder or grains which have been purchased on the market as the hydrogen occluding metal may be employed.

The type of the binder may be arbitrarily be selected if the selected binder is able to bind hydrogen occluding metal. When the binder is made of a powder material or a porous material, hydrogen passes through spaces among binder particles. The material of the binder may have a hydrogen transmission characteristic.

It can be considered that when the binder is made of a material which does not substantially permit transmission of hydrogen, the network among hydrogen occluding metal particles causes all of hydrogen occluding metal to uniformly occlude hydrogen.

The expansion and contraction of the hydrogen occluding Metal results in change in the distances between the hydrogen occluding metal particles. As a result, change in the resistance occurs. Therefore, it is preferable that an elastic material is employed to make the binder. The foregoing material is exemplified by fluorine resin which is a physically and chemically stable material. In an embodiment of the present invention, which will be described later, teflon powder (trade name which is hereinafter called "PTFE") is employed.

When PTFE is employed to serve as the binder, it is preferable that the mixture ratio of the hydrogen occluding metal (which is $LaNi_5$ in the embodiment) and PTFE is 5 to 1:1, more preferably 4 to 1.5:1 and most preferably 2:1.

The foregoing mixture ratio of PTFE and $LaNi_5$ applies to a binder and hydrogen occluding metal which are made of other materials.

When PTFE is employed to serve as the binder, the relationship between the resistance value of the sensor body and the quantity of hydrogen occluded in the hydrogen occluding metal is as shown in FIG. 2. The abscissa of the graph shown in FIG. 2 stands for the quantity of hydrogen which can be occluded in the hydrogen occluding metal and which is 1.0. When the quantity of occluded hydrogen is zero, the maximum quantity is 0.0. As can be understood from the relationship shown in FIG. 2 between the resistance values of the sensor body and the quantities of hydrogen, the rate of change in the resistance value (which is a logarithmic value) is raised in a region in which the quantity of hydrogen is small.

When fine powder is mixed with the binder, the relationship between the quantity of hydrogen and the resistance value can be varied. The fine powder may be conductive powder, such as carbon powder, aluminum powder or iron powder, insulating powder of alumina, silica or magnesia or other semiconductor powder. The particle size of the powder must be smaller than that of the hydrogen occluding metal. It is preferable that the former particle size is not larger than 1/5 to 1/10 of the particle size of the latter material.

The relationship between the resistance of the sensor body and the quantity of hydrogen realized after 5 wt % to 20 wt % carbon powder has been added to the hydrogen occluding metal is shown in FIG. 3. As shown in FIG. 3, the resistance value (the logarithmic value) always has a predetermined rate of change regardless of the quantity of hydrogen.

The conductive carbon powder flattens the irregular surface of the hydrogen occluding metal particles. As a result, substantially constant area of contact among hydrogen occluding metal particles can be maintained. Therefore, the contact resistance is not substantially changed. Thus, it can be considered that only the number of contacts of the hydrogen occluding metal exerts an influence on the change in the resistance value.

When 5 wt % to 30 wt % fine insulating powder of alumina or the like is added to the hydrogen occluding metal, the relationship between the resistance of the sensor body and the quantity of hydrogen is as shown in FIG. 4. Since the fine powder having the insulating characteristic flattens the irregular surface of the hydrogen occluding metal, the area of the conductive surface of the hydrogen occluding metal is considerably reduced. Therefore, it can be considered that the contact resistance among the hydrogen occluding metal particles exerts a great influence in a range in which the quantity of hydrogen is small and the contact pressure is low.

The sensor body is formed as follows: initially the material for forming the binder is liquefied, followed by mixing powder of the hydrogen occluding metal. Then, the mixture is introduced into a cavity of a mold so that a required shape is formed.

When powder of PTFE or the like is employed to form the binder, the powder and the hydrogen occluding metal are mixed with each other, followed by sintering or hot-pressing the mixture so that the binder is formed.

Another method may be employed with which the hydrogen occluding metal and powder of PTFE are suspended in liquid after which the suspended matter is dried (and sintered) so that the sensor body is formed.

FIG. 5 shows an example in which the conductive binder is employed.

Referring to FIG. 5, reference numeral 112a represents hydrogen occluding metal and 112b represents a porous conductive film made of a metal material, such as copper, to serve as the binder. The porous conductive film made of the metal is subjected to electrolytic plating or electroless plating so as to ensure that conductive films having the desired property of being considerably porous are formed. The porous film 112b formed has the characteristic for permitting transmission of hydrogen.

If the applied porous conductive film 112b has a large thickness, the electric conductivity of the film is made to be great. Therefore, the measurement of change in the resistance using expansion and contraction of the hydrogen occluding metal 112a cannot easily be performed.

If the conductive metal film for covering the hydrogen occluding metal has the characteristic for permitting transmission of hydrogen, the necessity of using the porous film can be eliminated. In the foregoing case, a pressing process or the like may be employed to form the thin conductive metal film on the surface of the hydrogen occluding metal.

In the case of FIG. 5 in which the foregoing structure serves as the sensor body, the relationship between resistance values and the quantities of hydrogen is as shown in FIG. 2.

In the case of FIG. 5, the metal film 112b serves as the binder to bind the hydrogen occluding metal. Therefore, necessity of using another binder can be eliminated. Therefore, a process of pressing the hydrogen occluding metal covered with the film 112b enables a sensor body having a required shape to be formed.

As a matter of course, employment of the above-mentioned insulating binder made of PTFE or the like and/or the fine powder is not limited.

The sensor body may have an arbitrary shape. For example, a square pole shape, a cylindrical shape or the like may be employed. A pair of electrodes are joined to the sensor body to measure the resistance between the two electrodes.

The method of joining the electrodes is not limited if ohmic contact is realized between the sensor body and the electrodes. To reduce the number of manufacturing process steps, It is preferable that a process is employed with which the electrodes are, as cores, embedded in the sensor body when the sensor body is molded. The sensor body and the electrodes may be connected with a conductive adhesive agent or the like.

BRIEF DESCRIPTION OF THE DRAWINGS

These and other objects and technical advantages of the present invention will be readily apparent from the following description of the preferred exemplary embodiments of the invention in conjunction with the accompanying drawings, in which:

FIGS. 1(A) and 1(B) show the structure of a sensor body and illustrate the mechanism of the relationship between resistance values and quantities of hydrogen, in which FIG. 1(A) is a conceptual diagram showing a state of the sensor body in which the hydrogen occluding metal has occluded hydrogen in a small quantity and FIG. 1(B) is a conceptual view showing a state of the sensor body in which the hydrogen occluding metal has occluded hydrogen in a large quantity;

DESCRIPTION OF THE PREFERRED EMBODIMENTS

Embodiments of the present invention will now be described.

Figure 1A:
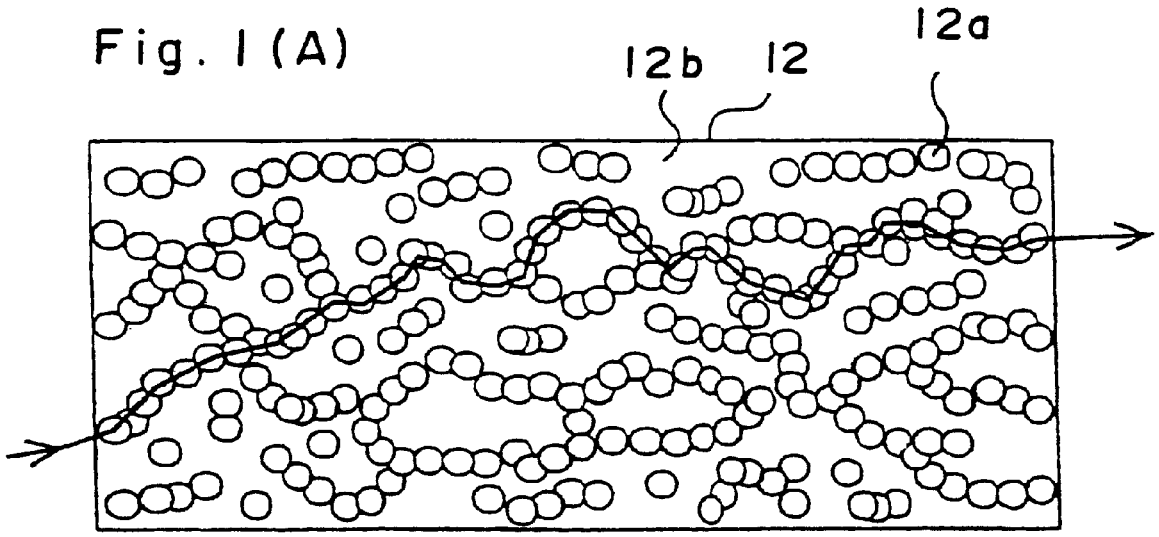
Figure 1B:
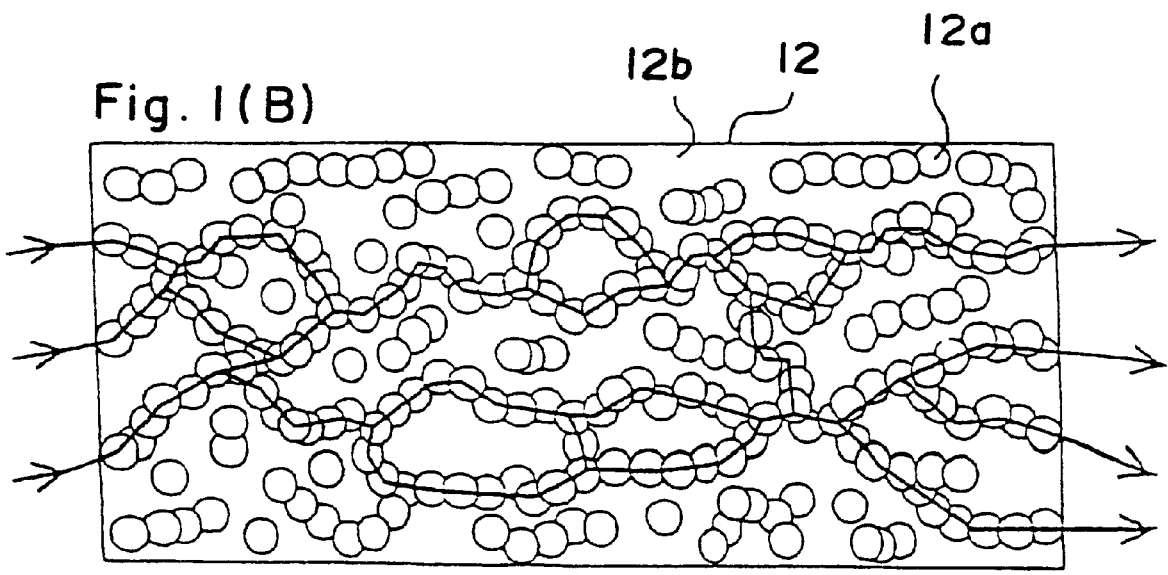
Figure 6:
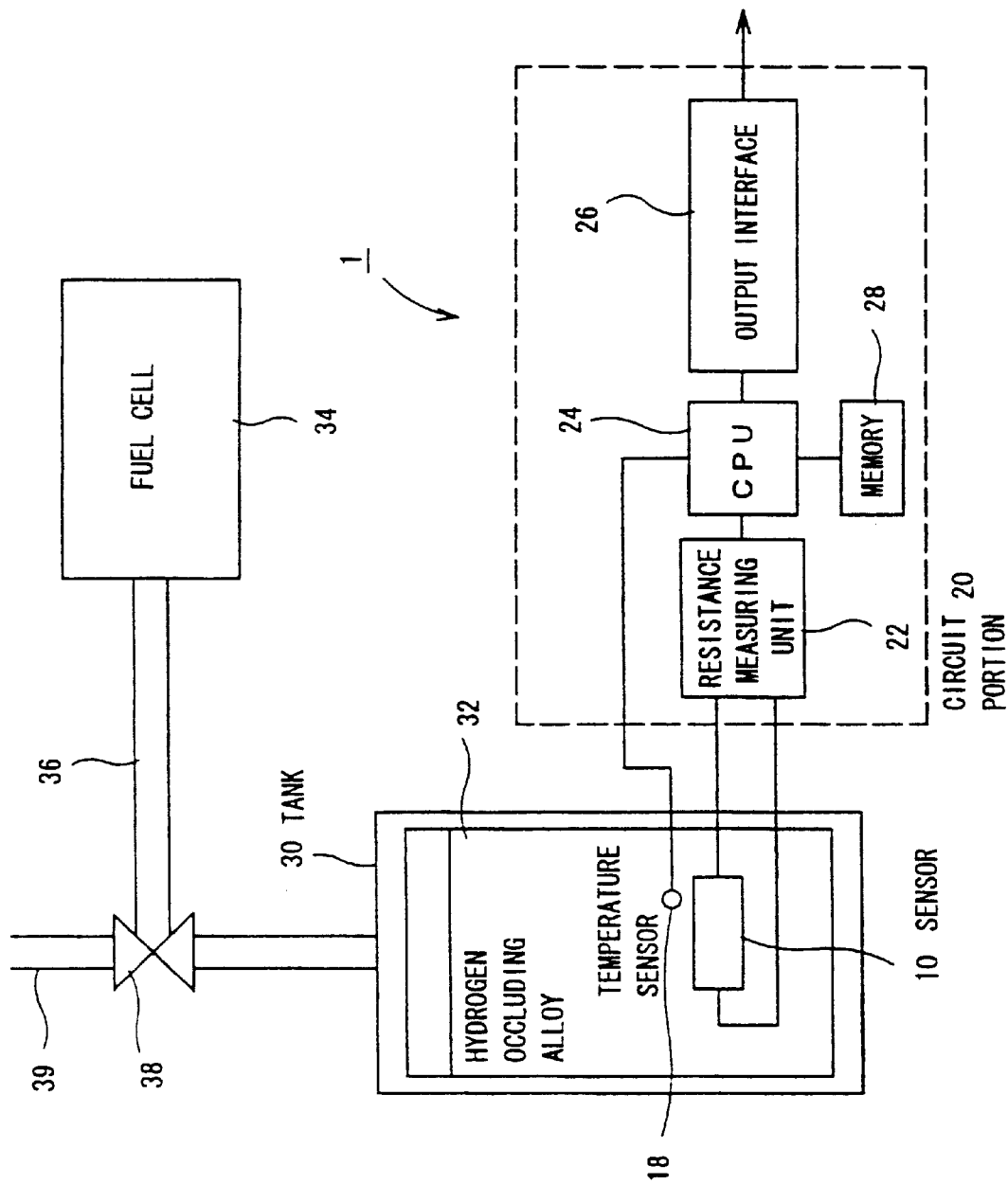
FIG. 6 is a diagram showing an apparatus for measuring the quantity of hydrogen according to a first embodiment of the present invention.

FIG. 6 shows the structure of an apparatus 1 for measuring the quantity of hydrogen incorporating the sensor body 12 shown in FIG. 1. As shown in FIG. 6, the apparatus 1 for measuring the quantity of hydrogen is mounted on an electric vehicle so as to measure a residual quantity of hydrogen in a tank 30 which accumulates hydrogen to supply hydrogen to a fuel cell 34 which serves as a power source.

The tank 30 accumulating hydrogen accommodates La type hydrogen occluding metal 32. Hydrogen is supplied to the fuel cell 34 through a supply pipe 36 and a valve 38.

The apparatus 1 for measuring the quantity of hydrogen incorporates a sensor 10, a temperature sensor 18 embedded in the hydrogen occluding metal 32 and a circuit portion 20 for calculating the quantity of hydrogen occluded in the tank 30 for accumulating hydrogen by measuring the resistance value of the sensor 10. The circuit portion 20 incorporates a resistance measuring unit 22 for measuring the resistance value of the sensor 10 by applying voltage (an electric current) to the sensor 10; a CPU 24 for calculating the quantity of hydrogen occluded in the tank 30 for accumulating hydrogen in accordance with the measured resistance value; a memory 28 for storing control information which is used by the CPU 24 and a data table to which a reference is made when the quantity of hydrogen is calculated; and an output interface 26 for communicating the quantity of hydrogen calculated by the CPU 24 to an ECU not shown for controlling the vehicle.

Figure 7:
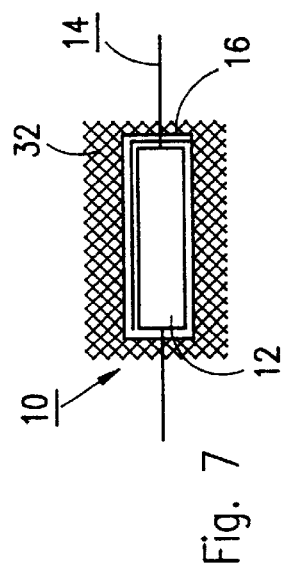
FIG. 7 is a diagram showing a sensor.

FIG. 7 shows the structure of the sensor 10. The sensor 10 incorporates a sensor body 12; collector electrodes 14 joined to two lengthwise directional ends of the sensor body 12; and an electrically insulating porous film 16 arranged to cover the sensor body 12 and the electrodes 14 and having a characteristic for permitting transmission of hydrogen.

Hydrogen occluding metal 12a for constituting the sensor body 12 is the same or the same type as the hydrogen occluding metal 32 in the tank 30 for accumulating hydrogen. The reason why the sensor 10 is embedded in the hydrogen occluding metal 32 in the tank 30 lies in that the hydrogen occluding metal 12a of the sensor 10 and the hydrogen occluding metal 32 in the tank 30 must have the same environment which exerts an influence on the hydrogen occluding characteristics, including the temperature and pressure.

Figure 8:
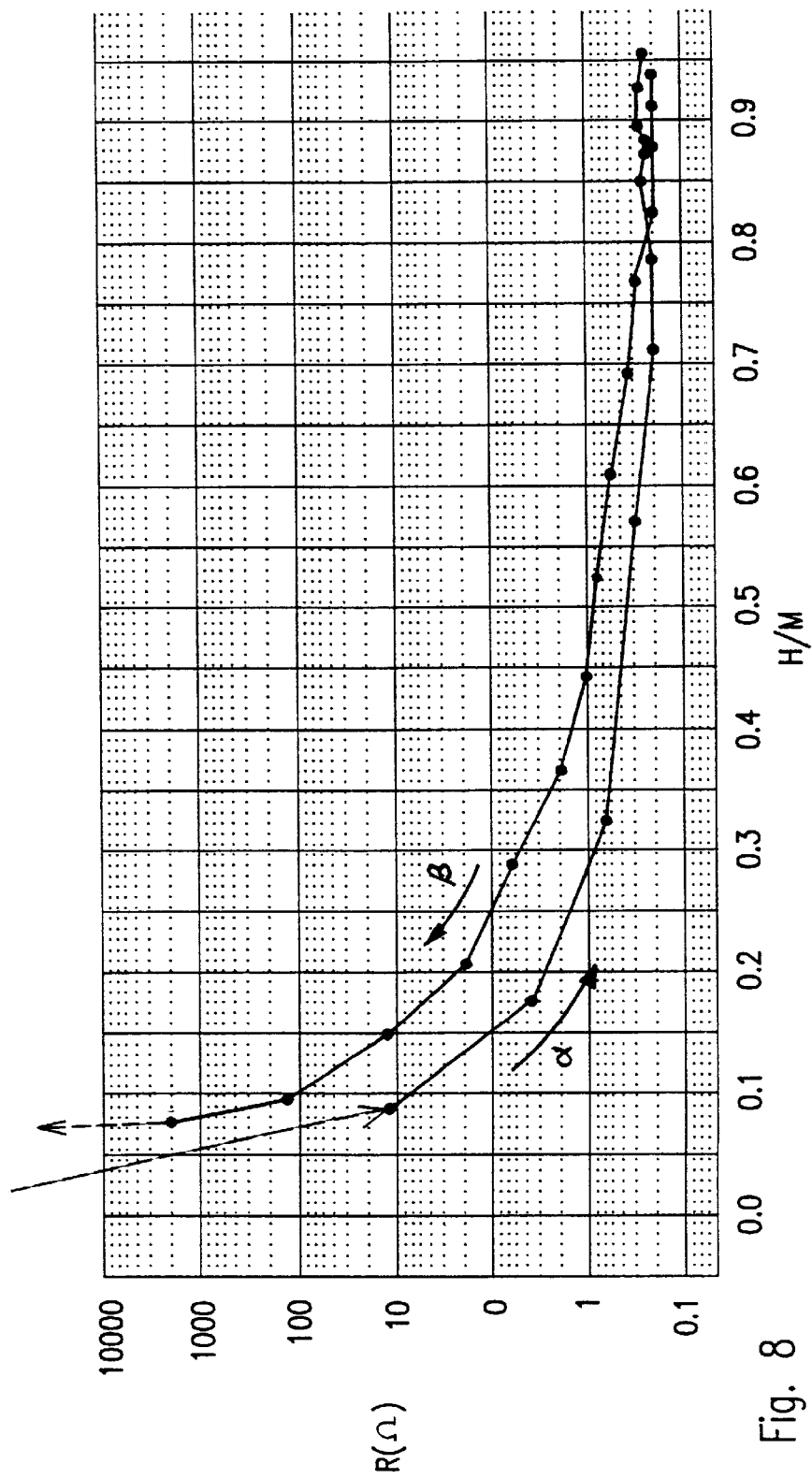
FIG. 8 is a graph showing the relationship between resistance values and quantities of hydrogen according to the embodiment.

Hydrogen occluding metal composed of 75 wt % hydrogen occluding metal (misch metal alloy manufactured by Japan Metals & Chemicals. Co., Ltd.) and 25 wt % PTFE (polyflon TFE M-12 manufactured by Daikin) were mixed. Then the mixture was burnt at 350° C. for 5 minutes, and then cut so that a sensor body 12 in the form of a 30 mm×5 mm×2 mm square pole was obtained. FIG. 8 shows the relationship between the electric resistance value of the sensor 10 incorporating the sensor body 12 and the quantity of hydrogen enclosed in the tank 30 for accumulating hydrogen.

The graph shown in FIG. 8 has an ordinate which stands for the resistance values Ω (logarithmic values) of the sensor 10 and an abscissa which stands for the quantities of hydrogen (when the value is 1.0, the quantity is full and when the quantity is 0.0, the quantity is empty). As shown in FIG. 8, the resistance value is reduced as the quantity of hydrogen is enlarged. When the quantity of hydrogen is reduced, the resistance value is enlarged. Note that change in the resistance value indicated with an arrow a is change in the resistance which occurs when the tank 30 for accumulating hydrogen is filled with hydrogen. Change in the resistance value indicated with an arrow β is change in the resistance which occurs when hydrogen in the tank 30 is discharged.

As described above, the change in the resistance occurring with respect to the quantity of hydrogen has hysteresis. The apparatus for measuring the quantity of hydrogen is arranged to determine whether hydrogen is being discharged from the tank 30 for accumulating hydrogen or hydrogen is being enclosed into the same in consideration of the hysteresis.

Figure 9:
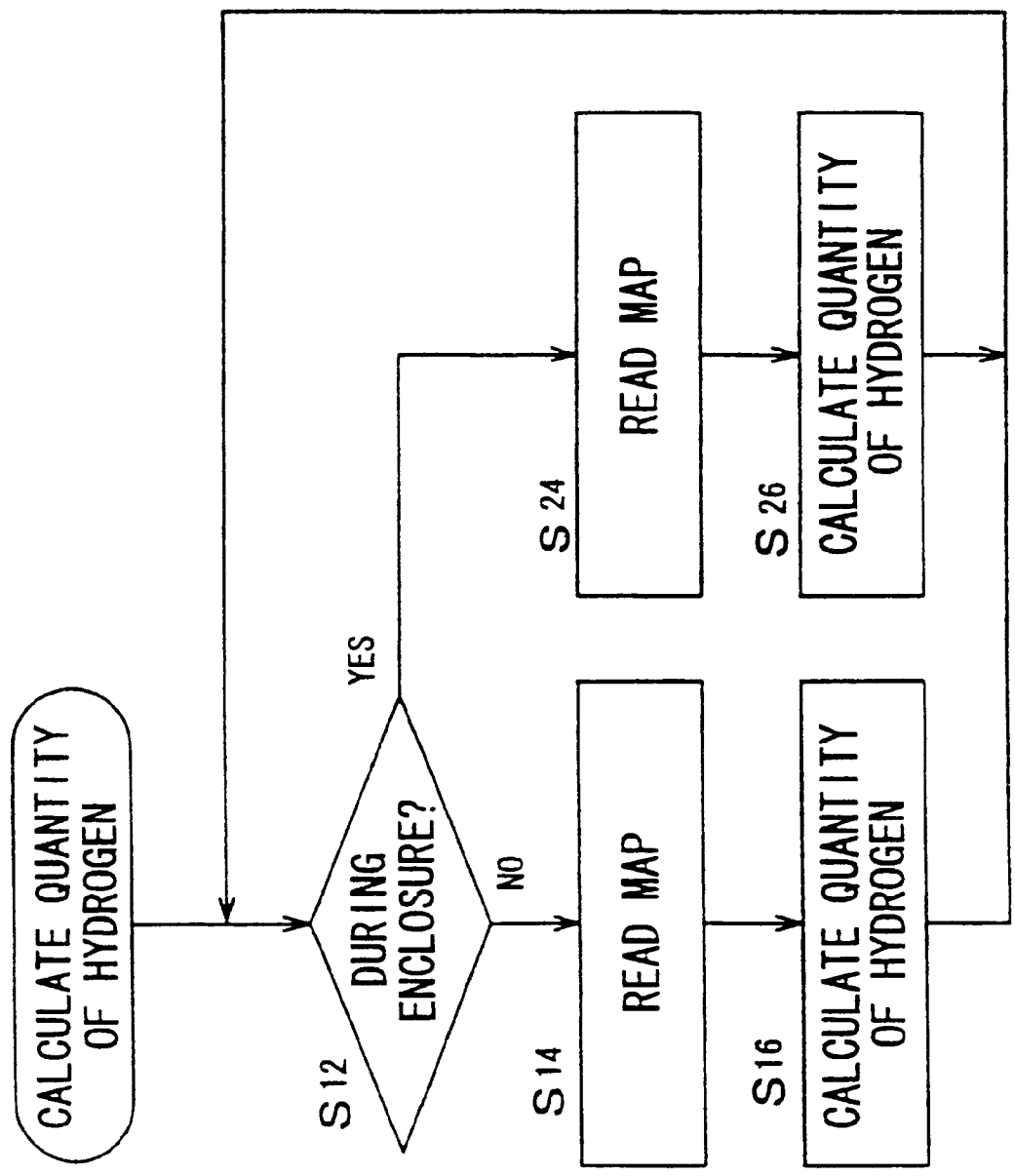
FIG. 9 is a flow chart showing the operation of the apparatus for measuring the quantity of hydrogen according to the first embodiment.

The operation of the apparatus 1 for measuring the quantity of hydrogen according to this embodiment will now be described with reference to a flow chart shown in FIG. 9.

The CPU 24 detects whether the valve 38 (see FIG. 6) opens to the supply pipe 36 adjacent to the fuel cell 34 or to the supply pipe 39 for adding hydrogen. In a state in which the former pipe is opened, the CPU 24 determines that hydrogen is being discharged. In a state in which the latter pipe is opened, the CPU 24 determines that hydrogen is being added (step S 12). The foregoing step constitutes a determining means.

During supply of hydrogen to the fuel cell 34 (No in step S12), the operation proceeds to step S14. In step S14 a data map is read which is in the form of a table showing the relationship of the arrow a shown in FIG. 8 at a temperature in the tank (which is measured by the temperature sensor 18). The resistance value of the sensor 10 is applied to the data map so that the quantity of hydrogen in the tank 30 for accumulating hydrogen is calculated.

During the introduction of hydrogen into the tank 30 for accumulating hydrogen (Yes in S12), the operation proceeds to step S24. In step S24 a data map is read which is in the form of a table showing the relationship of the arrow β shown in FIG. 8 at a temperature of the tank (which is measured by the temperature sensor 18). The resistance value of the sensor 10 is applied to the data map so that the quantity of hydrogen in the tank 30 for accumulating hydrogen is calculated.

The relationship shown in FIG. 8 is produced for each temperature in the tank 30 for accumulating hydrogen so as to be stored in the memory 28.

Figure 10:
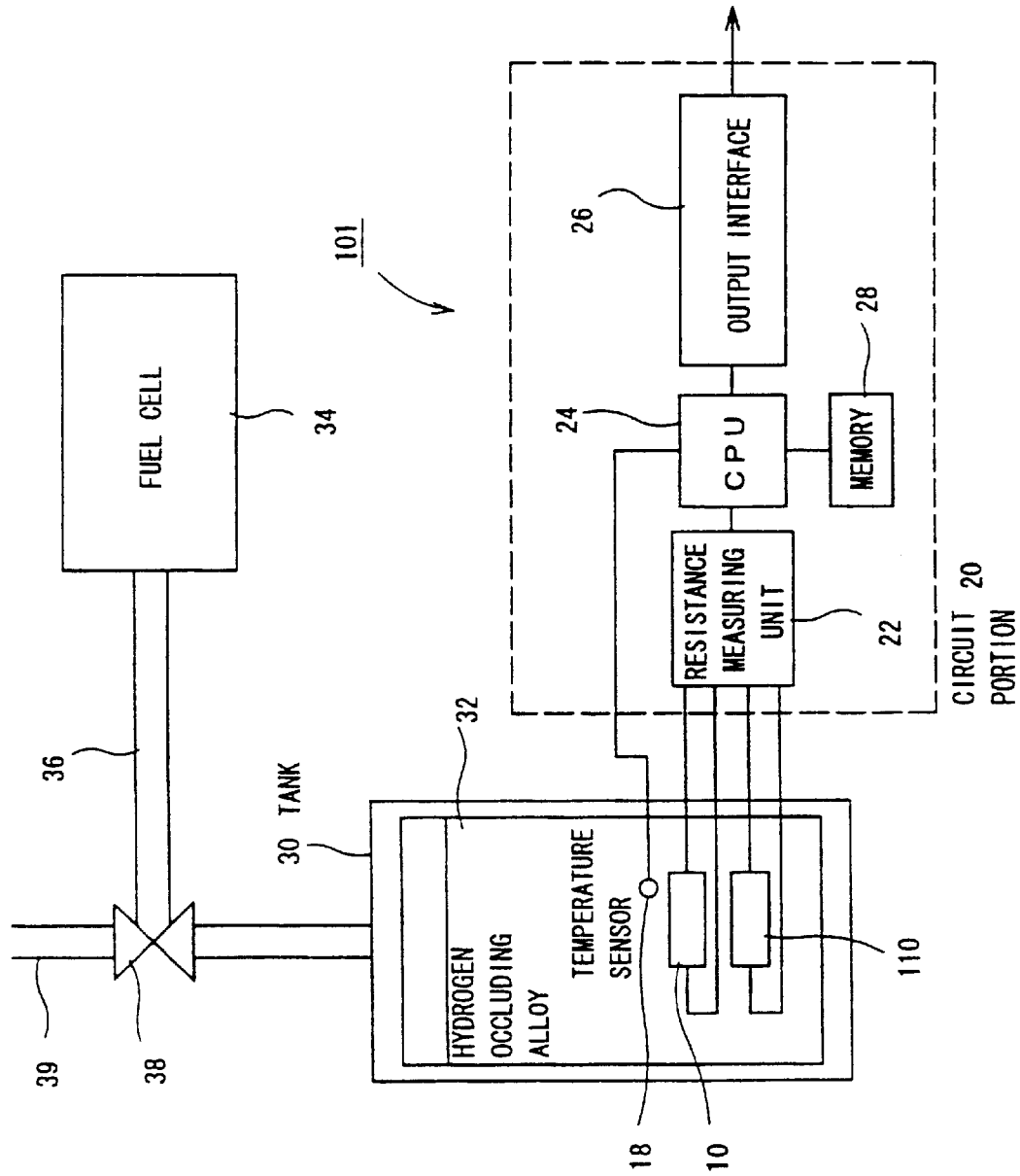
FIG. 10 is a diagram showing an apparatus for measuring the quantity of hydrogen according to a second embodiment of the present invention.
Figure 11:
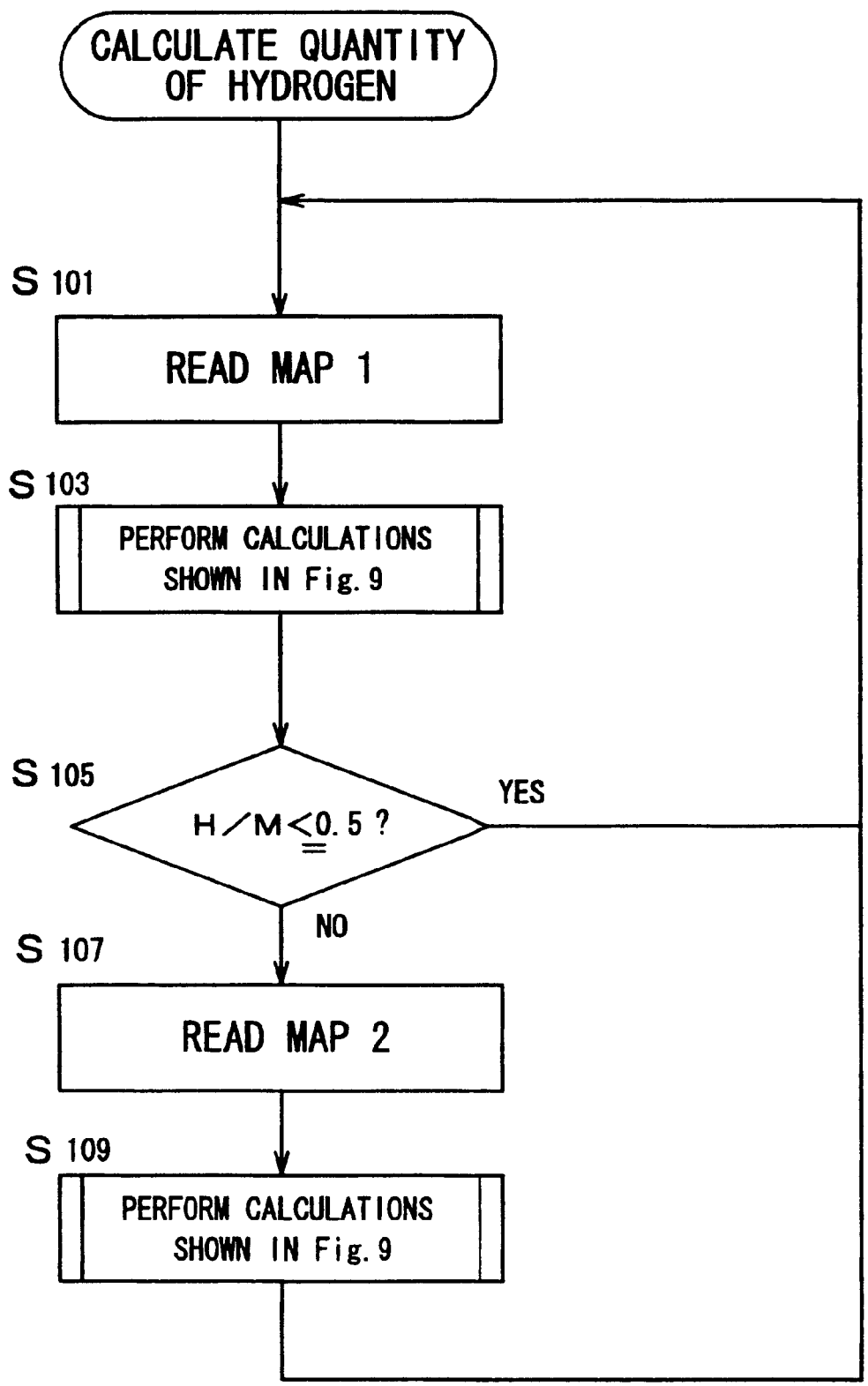
FIG. 11 is a flow chart showing the operation of the apparatus for measuring the quantity of hydrogen according to the second embodiment.

An apparatus 101 for measuring the quantity of hydrogen according to a second embodiment of the present invention will now be described with reference to FIGS. 10 and 11. In FIG. 10, the same elements as those shown in FIG. 6 are given the same reference numerals and the same elements are omitted from description.

Figure 4:
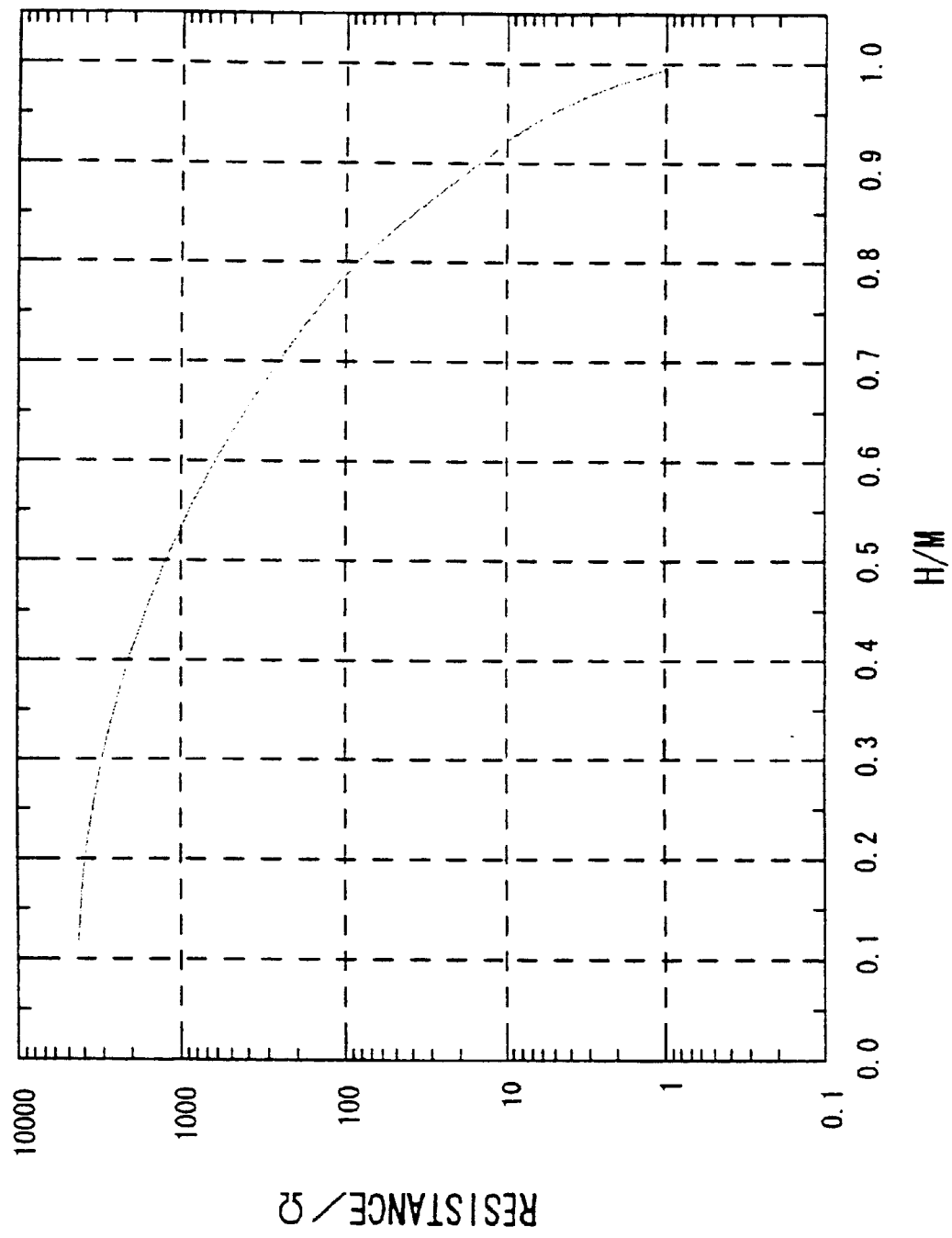
FIG. 4 is a graph showing the relationship between resistance values and quantities of hydrogen for another type sensor body.
Figure 5:
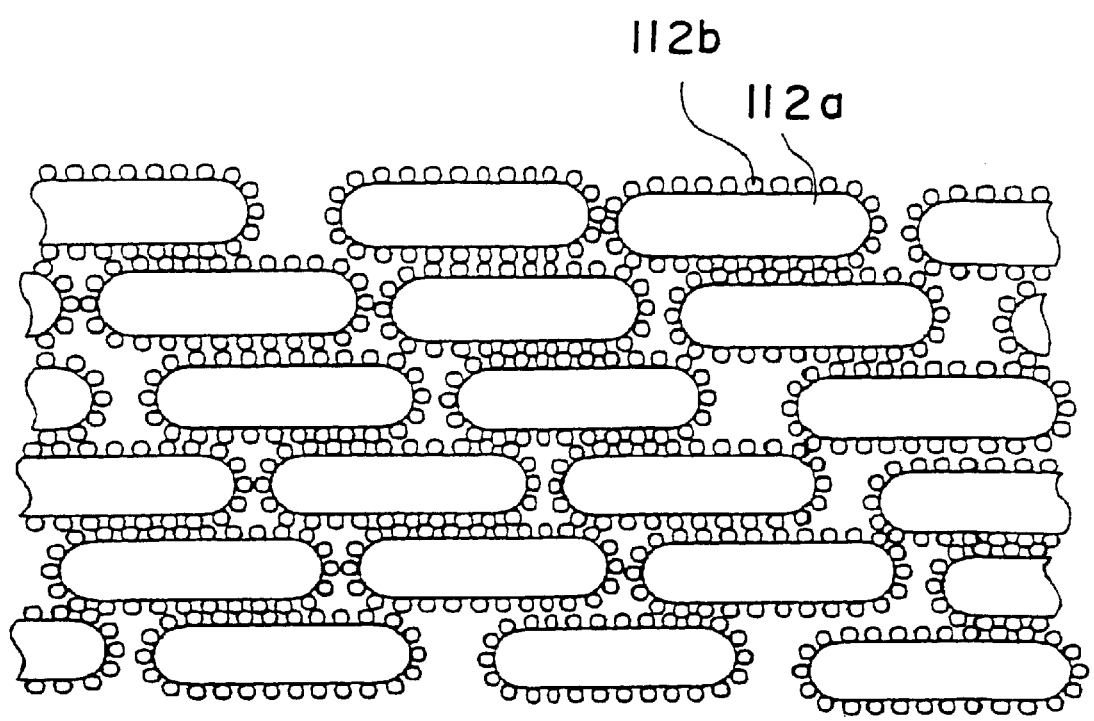
FIG. 5 is a conceptual view showing the structure of another type sensor body.

The apparatus 101 for measuring the quantity of hydrogen according to this embodiment incorporates two sensors 10 and 110 having different characteristic relationships between the resistance and the quantity of hydrogen. A data map corresponding to the characteristic of the second sensor 110 for each temperature is stored in the memory 28. The second sensor 110 has a sensor body formed by adding alumina powder to the binder, the alumina powder being the fine insulating powder. The other structures of the second sensor 110 are the same as those of the first sensor 10. The relationship between the resistance of the sensor body to which the alumina powder has been added and the quantity of hydrogen is as shown in FIG. 4. Also in the foregoing case, the relationship has hysteresis similar to that shown in FIG. 8.

The operation of the apparatus 101 for measuring the quantity of hydrogen according to this embodiment will now be described with reference to a flow chart shown in FIG. 11.

In step S101 the CPU 24 reads the data map corresponding to the first sensor 10 to store the data map in the buffer memory of the CPU 24. Then, the CPU 24 performs calculations shown in FIG. 9 (step S103). The data map for use in this process has been read in step S101.

In step S105 whether or not the quantity of hydrogen (H/M) obtained in step S103 is not higher than 0.5 is determined. If the quantity of hydrogen is 0.5 or lower (Yes in S105), the quantity of hydrogen obtained in step S103 is employed as a result of the measurement.

When the result obtained in step S103 is higher than 0.5 (No in S105), the operation proceeds to step S107. In step S107 the CPU 24 reads the data map corresponding to the second sensor 110 from the memory 28 so as to store it in the buffer memory of the CPU 24. Then, the calculations shown in FIG. 9 are performed (step S109). The data map for use in this process has beenreadinstepS107. A result obtained in step S109 is employed as a final result of the measurement.

As shown in FIG. 8, the first sensor 10 has a high rate of change in the resistance value (the logarithmic value) in a region in which the quantity of hydrogen is relatively small. On the other hand, the second sensor 110, as shown in FIG. 4, has a high ratio of change in the resistance value (the logarithmic value) in a region in which the quantity of hydrogen is relatively large. In this embodiment, a threshold value of 0.5 is employed for determining the quantity of hydrogen. If the quantity of hydrogen is smaller than the foregoing threshold value, the result of the measurement obtained by the first sensor 10 is employed. If the quantity of hydrogen is larger than the foregoing threshold value, the result of the measurement obtained by the second sensor 110 is employed. As a result, accurate measurement can be performed.

The threshold value may arbitrarily be determined. In this embodiment, the comparison is made between the threshold value and the result of the measurement obtained by the first sensor 10. As a matter of course, the result of the measurement obtained by the second sensor 110 and the threshold value may be subjected to a comparison.

Figure 2:
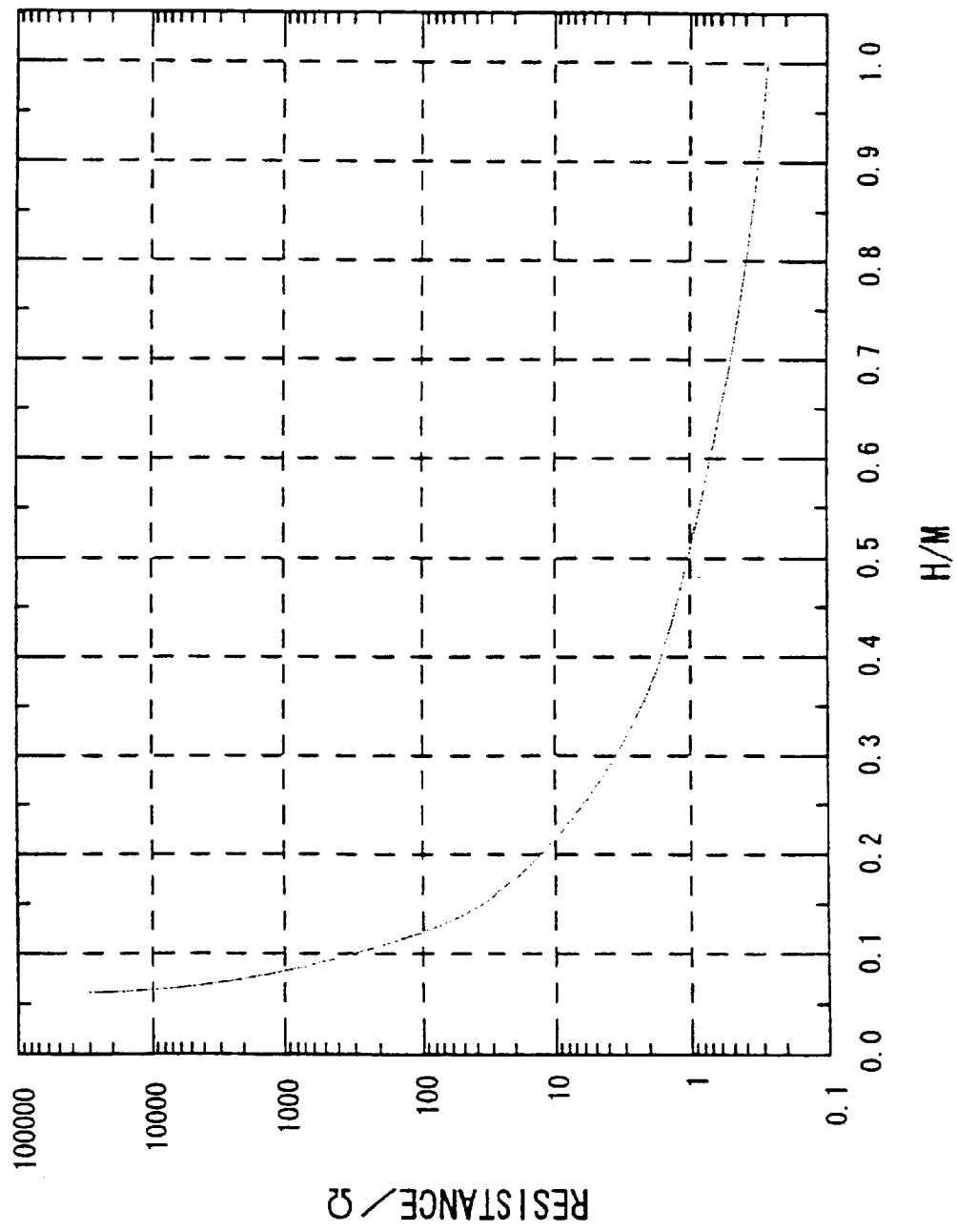
FIG. 2 is a graph showing the relationship between resistance values and quantities of hydrogen for a sensor body.
Figure 3:
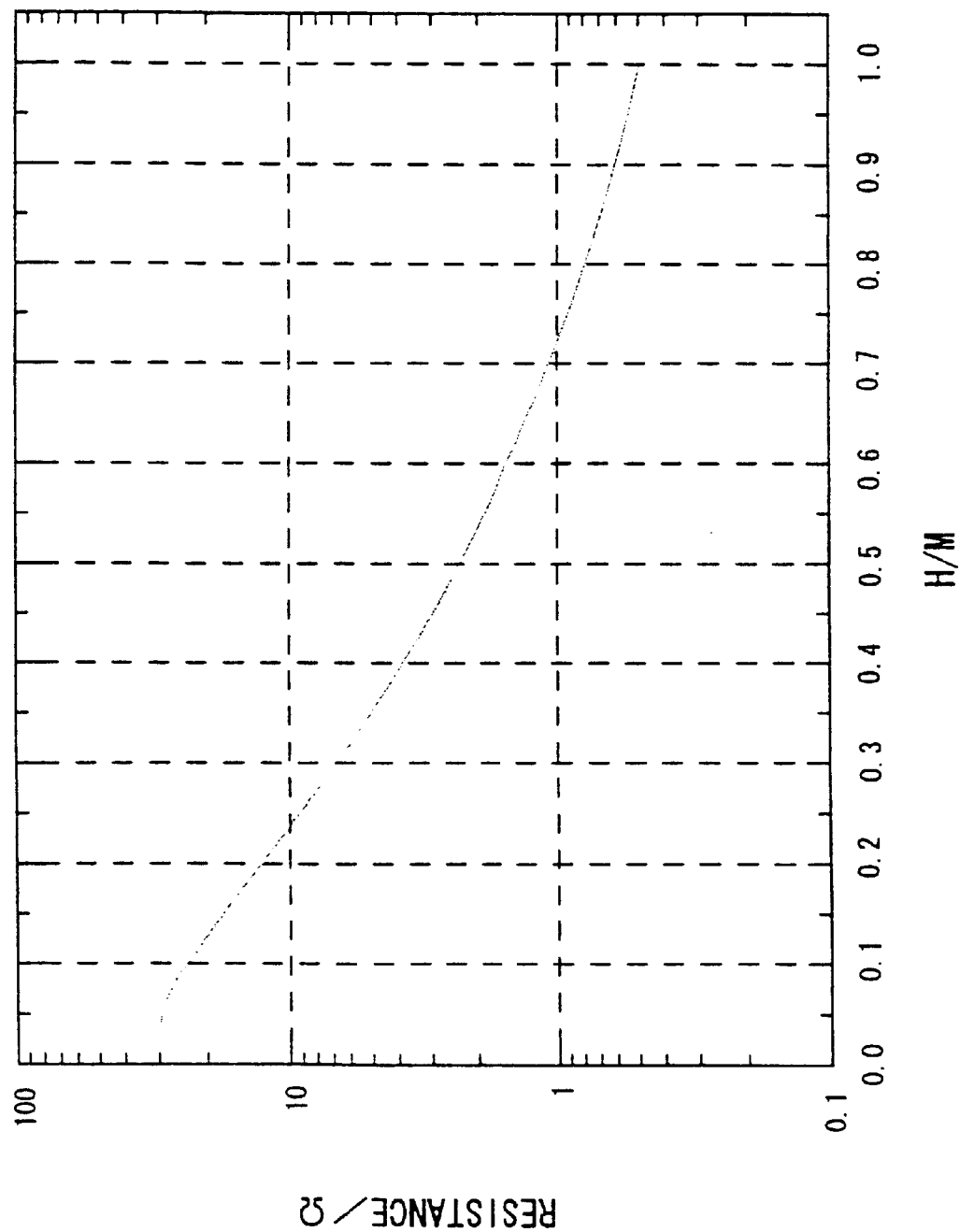
FIG. 3 is a graph showing the relationship between resistance values and quantities of hydrogen with another type sensor body.
Figure 12:
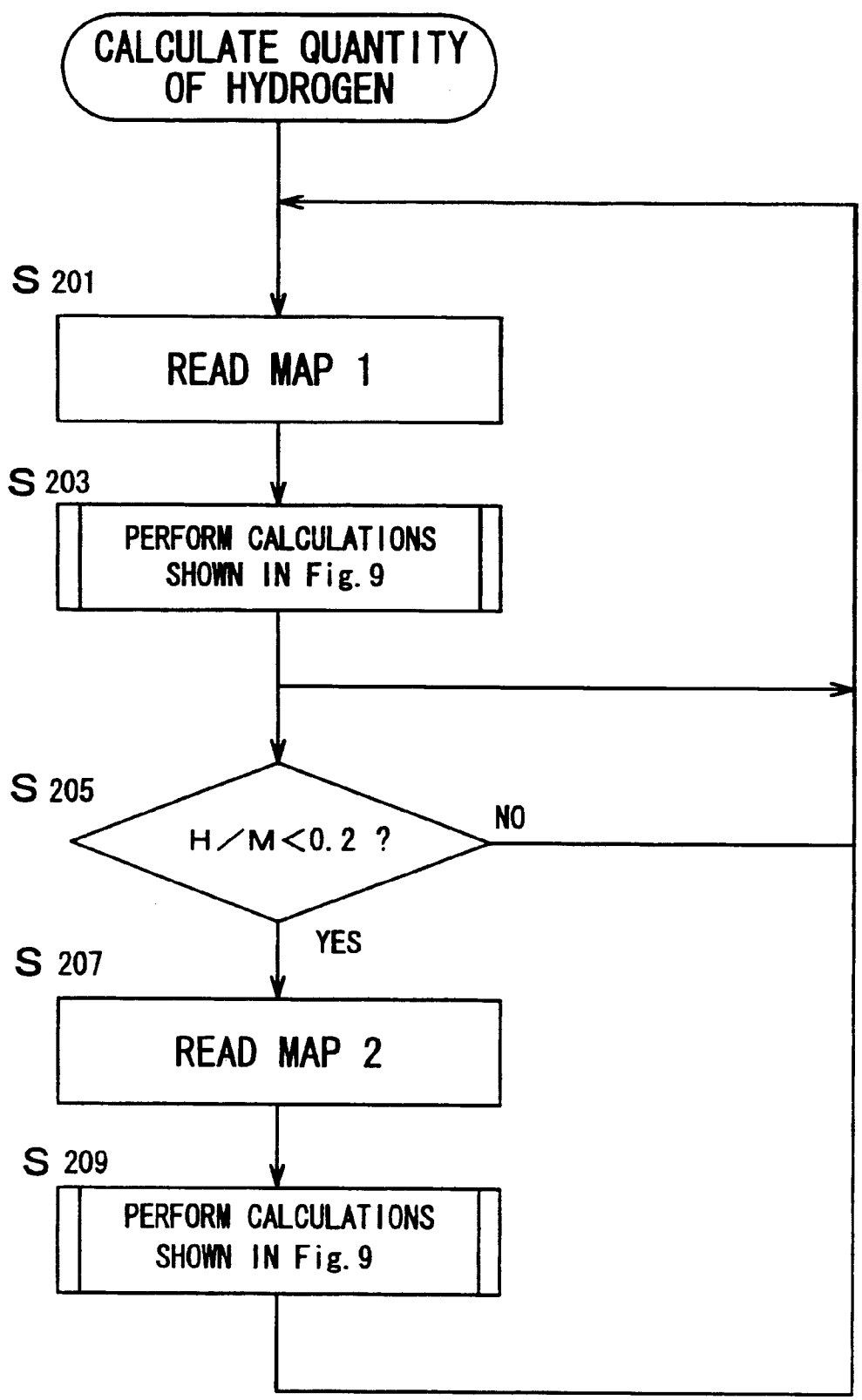
FIG. 12 is a flow chart showing another operation of the apparatus for measuring the quantity of hydrogen according to the second embodiment.

Another operation of the apparatus 101 for measuring the quantity of hydrogen according to the second embodiment will now be described with reference to a flow chart shown in FIG. 12. In the foregoing case, the relationship between the resistance value of the first sensor and the quantity of hydrogen is shown in FIG. 3. The relationship between the resistance value of the second sensor and the quantity of hydrogen is shown in FIG. 2. Each relationship has hysteresis.

In step S201 the CPU 24 reads the data map 1 corresponding to the first sensor from the memory 28 so as to store the data map in the buffer memory of the CPU 24. Then, the CPU 24 performs the calculations shown in FIG. 9 (step S203). A data map 1 for use in the foregoing process has been read in step S201. All of results of the measurement obtained in step S203 are employed.

In step S205 whether or not the quantity of hydrogen (H/M) obtained in step S203 is lower than 0.2 is determined.

If the result obtained in step S203 is lower than 0.2 (Yes in step S205), the operation proceeds to step S207. In step S207 the CPU 24 reads the data map 2 corresponding to the second sensor from the memory 28 so as to store the data map in the buffer memory of the CPU 24. Then, the CPU 24 performs the calculations shown in FIG. 9 (step S209). The data map 2 for use in the foregoing process has been read in step S207. Then, the CPU 24 subjects the result obtained in step S209 and the predetermined threshold value (for example, 0.1) to a comparison. When the result of the measurement is not higher than the threshold value, the CPU 24 determines that the quantity of hydrogen in the tank for accumulating hydrogen is substantially empty. Thus, the CPU 24 transmits a signal to the output interface 26. The output interface 26 transmits an output signal to a control unit of the vehicle to activate a display (empty lamp) in the vehicle.

In this embodiment, the measurement of the quantity of hydrogen in the tank for accumulating hydrogen is performed by using only the first sensor having the characteristic shown in FIG. 3. In FIG. 3, the resistance value (the logarithmic value) is changed substantially linearly with respect to the quantity of hydrogen. Therefore, the quantity of hydrogen can accurately be estimated for the overall region of the quantity of hydrogen.

The characteristic (see FIG. 2) of the second sensor having the resistance value (the logarithmic value) which is changed considerably in the region in which the quantity of hydrogen is small is used to generate an alarm signal. Since the alarm signal must have a satisfactory accuracy, it is preferable that the second sensor is employed.

Figure 13:
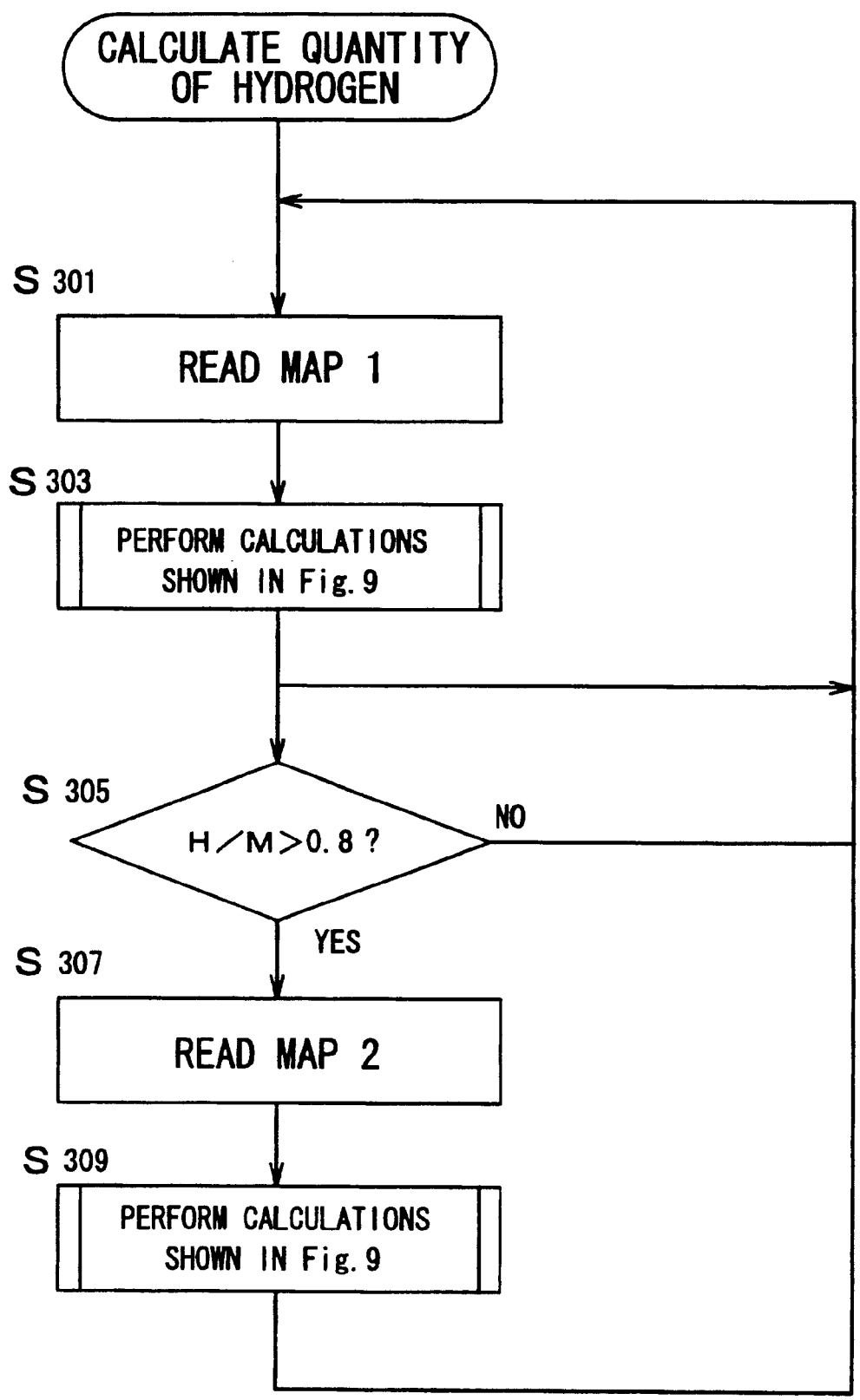
FIG. 13 is a flow chart showing another operation of the apparatus for measuring the quantity of hydrogen according to the second embodiment.

Another operation of the apparatus 101 for measuring the quantity of hydrogen according to the second embodiment will now be described with reference to a flow chart shown in FIG. 13. In the foregoing case, the characteristic of the first sensor for the relationship between the resistance value and the quantity of hydrogen is shown in FIG. 3. The characteristic of the second sensor for the relationship between the resistance value and the quantity of hydrogen is shown in FIG. 4. Each relationship has hysteresis.

In step S301 the CPU 24 reads the data map corresponding to the first sensor from the memory 28 so as to store the data map in the buffer memory of the CPU 24. Then, the CPU 24 performs the calculations shown in FIG. 9 (step S303). The data map for use in the foregoing process has been read in step S301. All of the results of the measurement obtained in step S303 are employed.

In step S305 whether or not the quantity of hydrogen (H/M) obtained in step S303 is higher than 0.8 is determined.

If a result in step S303 is higher than 0.8 (Yes in S305), the operation proceeds to step S307. Instep S307 the CPU 24 reads the data map corresponding to the second sensor from the memory 28 so as to store the data map in the buffer memory of the CPU 24. Then, the CPU 24 performs the calculations shown in FIG. 9 (step S309). The data map for use in the foregoing process has been read in step S307. The CPU 24 subjects a result obtained in step S309 and the predetermined threshold value (for example, 0.9) to a comparison. If the result of the measurement is larger than the threshold value, the CPU 24 determines that the quantity of hydrogen in the tank for accumulating hydrogen is substantially the upper limit. Thus, the CPU 24 transmits a signal to the output interface 26. The output interface 26 transmits, to a hydrogen supply source (connected to the base portion of the pipe 39 shown in FIG. 10), an alarm signal indicating the fact that the quantity of hydrogen in the tank for accumulating hydrogen is in a substantially full state.

In the foregoing case, the measurement of the quantity of hydrogen in the tank for accumulating hydrogen is performed by only the first sensor having the characteristic shown in FIG. 3. In FIG. 3, the resistance value (the logarithmic value) is changed substantially linearly with respect to the quantity of hydrogen. Therefore, the quantity of hydrogen can accurately be estimated for the overall region of the quantity of hydrogen.

The characteristic (see FIG. 4) of the second sensor giving a relationship between the resistance value (the logarithmic value) which is considerably changed in the region in which the quantity of hydrogen is large is used to generate an alarm signal. Since the alarm signal must have a satisfactory accuracy, it is preferable that the second sensor is employed.

In the foregoing description, the sensor according to the present invention is employed to estimate the quantity of hydrogen in the tank for accumulating hydrogen. Note that the sensor according to the present invention may be employed to measure the quantity of occluded hydrogen in a variety of materials. For example, the sensor can be employed to measure the quantity of charge (the quantity of occluded hydrogen) of a nickel-hydrogen cell. If a hydrogen occluding substance, which must be measured, and hydrogen occluding metal have similar hydrogen occluding characteristics, the sensor according to the present invention may be employed for any hydrogen occluding substance, including a bulk material, as well as the powder or granular material. Although the sensor is, in the foregoing embodiments, embedded in the hydrogen occluding metal in the tank for accumulating hydrogen, the position of the sensor is not limited if the sensor is, in the hydrogen occluding tank, exposed to the same environment as that for the hydrogen occluding metal.

It is understood that the present disclosure of the preferred form can be changed in the details of construction and in the combination and arrangement of parts without departing from the spirit and the scope of the invention.

We claim:

1. A sensor comprising:
   a unitary sensor body of particles of a hydrogen occluding metal dispersed within a binder, said sensor body having an electrical resistance along a variable path thru said sensor body depending upon a change in electrical contact resistance between said particles which varies in accordance with quantity of hydrogen occluded within said metal; and
   electrodes joined to said sensor body.

2. A sensor according to claim 1, wherein said binder permits transmission of hydrogen.

3. A sensor according to claim 1, wherein said binder is an insulating material.

4. A sensor according to claim 3, wherein powder or grains of fluorine resin is employed as said binder, and said binder and hydrogen occluding metal form said sensor body.

5. A sensor according to claim 3, wherein said binder is admixed with a conductor having a particle size smaller than the particle size of said hydrogen occluding metal.

6. A sensor according to claim 4, wherein said binder is admixed with carbon particles having a particle size which is smaller than the particle size of said hydrogen occluding metal.

7. A sensor according to claim 3, wherein said binder is admixed with an insulating material having a particle size which is smaller than the particle size of said hydrogen occluding metal.

8. A sensor according to claim 1, wherein said binder is a conductor.

9. A sensor according to claim 8, wherein said sensor body is formed by coating the surface of the particles of said hydrogen occluding metal with metal films.

10. A sensor according to claim 9, wherein said metal film is formed by plating.

11. A sensor comprising particles of a hydrogen occluding metal dispersed in a binder, wherein the electric resistance of said sensor along a variable path thru the sensor volume depending upon a change in electrical contact resistance between said particles corresponds to the quantity of hydrogen occluded in said hydrogen occluding metal.

12. A sensor according to claim 11, wherein said binder permits transmission of hydrogen.

13. A sensor according to claim 10, wherein the electric resistance corresponds to the quantity of hydrogen occluded in said hydrogen occluding metal in accordance with a first relationship when said quantity is within a first range, and
   the electric resistance corresponds to the quantity of hydrogen occluded in said hydrogen occluding metal in accordance with a second relationship, different from said first relationship, when said quantity is within a second range, different from said first range.

14. A sensor according to claim 13, wherein the quantity of hydrogen occluded in said hydrogen occluding metal in the second range is larger than the quantity in the first range.

15. A sensor according to claim 13, wherein the quantity of hydrogen occluded in said hydrogen occluding metal in the first range is larger than the quantity in the second range.

16. A sensor according to claim 10, wherein the electric resistance has the same relationship with the quantity of hydrogen occluded in said hydrogen occluding metal, for all quantities of hydrogen occluded in said hydrogen occluding metal.

17. A tank for accumulating hydrogen comprising said sensor according to claim 1.

18. A tank for accumulating hydrogen according to claim 17, further comprising means for calculating the quantity of hydrogen stored in said tank from an output from said sensor.

19. An apparatus for measuring the quantity of hydrogen occluded in a hydrogen occluding metal, comprising:
   a unitary sensor body of particles of the hydrogen occluding metal dispersed within a binder, said sensor body having an electrical resistance along a variable path thru said sensor body depending upon a change in electrical contact resistance between said particles which varies in accordance with quantity of hydrogen occluded within said metal;
   a pair of electrodes joined to said sensor body; and
   means for measuring an electrical resistance value between said electrodes.

20. An apparatus for measuring the quantity of hydrogen according to claim 19, further comprising calculating means for calculating the quantity of hydrogen in said hydrogen occluding metal basing on said resistance value.

21. An apparatus for measuring the quantity of hydrogen according to claim 19, further comprising:
   determining means for determining whether said hydrogen occluding metal is in a hydrogen occluding state or a hydrogen discharge state; and
   calculating means for, with reference to a first predetermined relationship, calculating the quantity of hydrogen in said hydrogen occluding metal in accordance with the resistance value when said hydrogen occluding metal is in the hydrogen occluding state.

22. An apparatus for measuring the quantity of hydrogen according to claim 19, further comprising:
   determining means for determining whether or not said hydrogen occluding metal is in a hydrogen occluding state or a hydrogen discharge state; and
   calculating means for, with reference to a second predetermined relationship, calculating the quantity of hydrogen in said hydrogen occluding metal in accordance with the resistance value when said hydrogen occluding metal is in the hydrogen discharge state.

23. An apparatus for measuring a quantity of hydrogen, comprising:
   a first measuring unit including a first unitary sensor body of particles of a hydrogen occluding metal dispersed within binder and which has an electrical resistance which varies in accordance with a first relationship with the quantity of hydrogen in said hydrogen occluding metal, and first calculating means for, with reference to the first relationship and in accordance with the electric resistance, calculating the quantity of hydrogen in said hydrogen occluding metal;
   a second measuring unit including a second unitary sensor body of particles of a hydrogen occluding metal dispersed within binders and which has an electrical resistance which varies in accordance with a second relationship with the quantity of hydrogen in said hydrogen occluding metal, and second calculating means for, with reference to the second relationship and in accordance with the electric resistance of said second sensor body, calculating the quantity of hydrogen in said hydrogen occluding metal; and
   an output unit for processing results of calculations performed by said first and second measuring units in accordance with a predetermined third relationship between electrical resistance and the quantity of hydrogen in said hydrogen occluding metal and outputting the result of the processing.

24. An apparatus for measuring a quantity of hydrogen according to claim 23, wherein
   in the first relationship the electric resistance varies with a first fashion of change with quantity of occluded hydrogen when the quantity of hydrogen in said hydrogen occluding metal is within a first range, and the electric resistance varies with a second fashion of change with quantity of occluded hydrogen, which is higher than that of the first fashion of change, when the quantity of hydrogen in said hydrogen occluding metal is within a second range in which the quantity of hydrogen in said hydrogen occluding metal is larger than the quantity in said first range,
   in the second relationship the electric resistance varies in a third fashion of change with quantity of occluded hydrogen, when the quantity of hydrogen in said hydrogen occluding metal is within the first range, and the electric resistance varies with a fourth fashion of change with quantity of occluded hydrogen, which is lower than the third fashion of change, when the quantity of hydrogen in said hydrogen occluding metal is within the second range, and
   said output unit employs the result of the calculation performed by said second unit when the quantity of hydrogen in said hydrogen occluding metal is within the first range and employs the result of the calculation performed by said first measuring unit when the quantity of hydrogen in said hydrogen occluding metal is within the second range.

25. An apparatus for measuring the quantity of hydrogen according to claim 23, wherein
   in the first relationship the electric resistance varies with quantity of hydrogen in the same fashion of change, regardless of the quantity of hydrogen occluded in said hydrogen occluding metal,
   in the second relationship the electric resistance varies in accordance with quantity of occluded hydrogen in a first fashion of change when the quantity of hydrogen in said hydrogen occluding metal is within a first range and the electric resistance varies in accordance with quantity of hydrogen in a second fashion of change which is higher than the first fashion of change, when the quantity of hydrogen in said hydrogen occluding metal is within a second range in which the quantity of hydrogen in said hydrogen occluding metal is larger than the quantity in said first range, and
   said output unit generates an alarm signal in accordance with the measurement performed by said second measuring unit when the measurement performed by said first measuring unit is for the second range.

26. An apparatus for measuring the quantity of hydrogen according to claim 23, wherein
   in the first relationship the electric resistance varies with quantity of hydrogen in the same fashion of change, regardless of the quantity of hydrogen occluded in said hydrogen occluding metal,
   in the second relationship the electric resistance varies in accordance with the quantity of occluded hydrogen in a first fashion of change, when the quantity of hydrogen in said hydrogen occluding metal is within a first range, and the electric resistance varies in accordance with quantity of hydrogen in a second fashion of change which is lower than the first fashion of change, when the quantity of hydrogen in said hydrogen occluding metal is within a second range in which the quantity of hydrogen in said hydrogen occluding metal is larger than the quantity in said first range, and said output unit generates an alarm signal in accordance with the measurement performed by said second measuring unit when the measurement performed by said first measuring unit is for the first range.

27. A method of measuring the quantity of hydrogen comprising steps of:

measuring electrical resistance of a unitary sensor body of particles of hydrogen occluding metal dispersed within a binder, said sensor body having an electrical resistance along a variable path thru said sensor body depending upon a change in electrical contact resistance between said particles which varies in accordance with quantity of hydrogen occluded within said metal; and calculating the quantity of hydrogen occluded in said hydrogen occluding material by applying the result of the measurement to a predetermined relationship between the electrical resistance and quantity of occluded hydrogen.

28. A tank according to claim 17, wherein said sensor is embedded in said hydrogen occluding metal in said tank, and said hydrogen occluding metal in the sensor body is the same as said hydrogen occluding metal in said tank.

29. A sensor according to claim 11, wherein the rate of change in the electric resistance increases as the quantity of hydrogen occluded in said hydrogen occluding metal is reduced.

30. A sensor according to claim 11, wherein the rate of change in the electric resistance decreases as the quantity of hydrogen occluded in said hydrogen occluding metal is reduced.

31. A sensor according to claim 11, wherein the rate of change in the electric resistance is constant regardless of the quantity of hydrogen occluded in said hydrogen occluding metal.

32. A sensor according to claim 29, wherein the rate of change in the electrical resistance is a logarithmic value of quantity of occluded hydrogen.

* * * * *